United States Patent [19]

Stolowitz

[11] Patent Number: 4,812,532

[45] Date of Patent: Mar. 14, 1989

[54] SOLID PHASE OXIME REAGENT

[75] Inventor: Mark L. Stolowitz, Long Beach, Calif.

[73] Assignee: Bio-Affinity Systems, Inc., Torrance, Calif.

[21] Appl. No.: 79,258

[22] Filed: Jul. 29, 1987

[51] Int. Cl.$^4$ .............................. C08G 69/48
[52] U.S. Cl. .................... 525/420; 436/111; 436/172; 525/419; 528/322
[58] Field of Search ............... 525/419, 420; 528/322

[56] References Cited

U.S. PATENT DOCUMENTS 4,115,305 9/1978 Hornby et al. ............... 525/419

Primary Examiner—Harold D. Anderson
Attorney, Agent, or Firm—Blakely, Sokoloff Taylor, Zafman

[57] ABSTRACT

A solid phase oxime compound having the general formula:

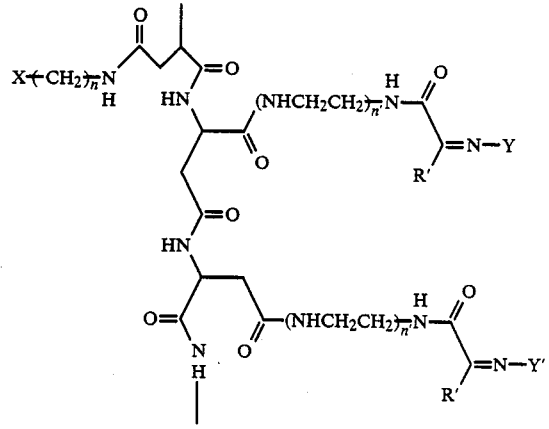

where X is particulate silica gel or controlled pore glass; n is 3 or 4, n' is 1-6; R' is an electron withdrawing group; and Y and Y' are selected from OH, OCOR", OSO$_2$R" and OCO$_2$R", where R" is a chromophore, fluorophore or electrophore, is disclosed. Also disclosed is the method for making compounds of this type and the method for using these compounds to detect and quantify analytes having primary or secondary amines or thiol functionalities.

18 Claims, No Drawings

SOLID PHASE OXIME REAGENT

FIELD OF THE INVENTION

This invention relates to the field of bioanalytical separation technology, and more particularly, to a new class of reactive solid phase reagents useful in inter alia, amino acid analysis, the method of preparing said reagents, and the method of using said reagents for the detection of mild nucleophilic species.

BACKGROUND OF THE INVENTION

A variety of polymeric reagents including solid phase activated esters and anhydrides have been prepared for use in the derivatization of amino acids (Kalir, R., Warshawsky, A., Fridkin, M., and Patchornik, A., Eur. J. Biochem., 59, 55 (1975)., Cohen, B. J., Hafeli, H. K., and Patchornick, A., J. Org. Chem., 49, 922 (1984)., Shambhu, M. B., and Digenis, G. A., J. Chem. Soc. Chem. Commun., 619 (1974)., Martin, G. E. et al, J. Org. Chem., 43, 4571 (1978)., Martin, G. E., Shambu, M. B., and Digenis, G. A., J. Pharm. Sci., 67, 110 (1978)., Shambhu, M. B. and Digenis, G. A., Tetrahedron Lett., 18, 1627 (1973)). These polymeric reagents are, to varying degrees, structurally related to the original Merrified polymeric reagents used in the synthesis of peptides. Certain classes of polymeric activated esters and anhydrides are unique in that they are able to selectively transfer an attached moiety to mild nucleophilic species (amines, amino acids and thiols) under relatively mild reaction conditions. This moiety may then be exploited as a basis for the separation and subsequent detection of the nucleophile.

Although the synthetic organic literature contains numerous examples of the use of supported reagents for a variety of applications, examples of the use of immobilized reagents or solid phase reagents (SPR) for the derivatization of compounds of interest (analytes) for subsequent analysis by high pressure liquid chromatography (HPLC) are limited (Krull, I. S. et al, J. Liq. Chromatogr., 6, 605 (1983)., Krull, I. S. et al, J. Liq. Chromatogr., 6, 1015 (1983)., Krull, I. S. et al, J. Liq. Chromatogr., 6, 2190 (1983)., Xie, K.-H., Colgan, S. and Krull, S. I., J. Liq. Chromatogr., 6(S-2), 125 (1983)., Nondek, L., Brinkman, U. A. T., and Frei, R. W., Anal. Chem., 55, 1466 (1983)., Nondek, L., Anal. Chem., 56 1194 (1984)., Bolme, M. W. and Langer, S. H., J. Phys. Chem., 87, 3366 (1983)., Vratny, P., Ouhrabkova, J., and Copikova, J., J. Chromatogr., 191, 313 (1980)., Nondek, L., Frei, R. W., and Brinkman, U. A. T., J. Chromatogr., 282, 141 (1983)., Studebaker, J. F., J. Chromatogr., 185, 497 (1979)., Lankmayr, E. P. et al, J. Chromatogr., 224 239 (1981)).

An solid phase reagent may be prepared on a variety of solid supports which may be inorganic or polymeric in nature, including silica, glass, alumina, Florisil, or various polymeric supports derived from polystyrene, polyacrylamide or polymethacrylate. The derivatizing moiety can be physically adsorbed, intercalated, or ionically or covalently bonded to the support. There are a number of significant advantages to performing solid phase derivatizations utilizing the foregoing reagents including (1) ease of separation of the supported species from the reaction mixture, (2) reuse of a supported reagent after regeneration, (3) adaptability to continuous flow processes, (4) reduced toxicity and odor of supported species compared with low molecular weight species, and (5) chemical differences, such as solubility or altered selectivity of a reagent (resulting from steric considerations), in supported form compared with its soluble analog.

However, polymeric supports exhibit properties which render them unsuitable for continuous flow processes in that they lack dynamic stability, by shrinking or swelling as a function of solvent polarity. This limits their potential for use in derivatizations wherein the SPR is confined to a column of predetermined volume (in-line). Additionally, only macroporous polymers, which are particularly costly, exhibit sufficient rigidity for use in high pressure chromatographic systems. Finally, those polymers which have been routinely utilized for the preparation of solid phase reagents exhibit considerable hydrophobic character which can result in the irreversible adsorption of an analyte.

Particulate silica and controlled pore glass are the supports of choice when rigidity and dynamic stability are required of a particular application. However, silica and glass exhibit adsorptive properties which render them inappropriate unless further functionalized. Bonded phase silica and controlled pore glass, prepared by reaction of the inorganic support with a functionalized alkylsilane, exhibit many of the required properties. In those situations in which adsorptive secondary interactions may prove particularly detrimental, as for example in the chromatography of biological molecules, a polymeric coating of bonded phase supports further removes secondary interactions. Particulate bonded silica has been coated with polyacrylamide, polyvinylalcohol, polyethyleneimine and polysuccinimide (Alpert, A. J., J. Chromatogr., 266, 23 (1983)., Alpert, A. J., J. Chromatogr., 359, 85 (1986)).

Therefore, it is desirable that solid phase reagents be provided which exhibit sufficient dynamic stability and rigidity, and lack deleterious adsorptive properties, for use in continuous derivatizations for the purpose of qualitative and quantitative identification of analytes by high pressure liquid chromatography.

SUMMARY OF THE INVENTION

The present invention relates to the preparation of solid phase reagents prepared from particulate silica gel or controlled pore glass. Particulate bonded phase silica gel or controlled pore glass containing aminopropyl or aminobutyl moieties is functionalized by reaction with poly(D,L-succinimide) to yield poly(D,L-succinimide)-silica which is further functionalized by reaction with a diamime or polyethyleneimine to yield alpha-beta-poly(aminoalkyl or polyiminoalkyl D,L-aspartamide)-silica. Reaction of an oxime prepared from the methyl, ethyl or activated ester of a substituted acetic acid bearing an electron withdrawing substituent results in a solid phase oxime. Subsequent reaction with an acid chloride or chloroformate yields the corresponding functionalized solid phase activated ester or carbonate which may then be employed in the derivatization of an analyte for subsequent analysis.

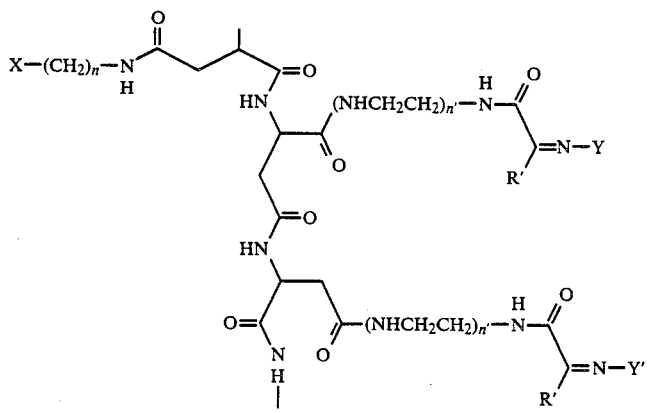

Formula I

The solid phase oxime reagents of the present invention are of the general formula I where X is particulate silica gel or controlled pore glass; n is 3 or 4, n' is 1–6, and preferably 2 or 3; R' is an electron withdrawing group, and preferably cyano, trifluoromethyl, trichloromethyl, dichloromethyl, chloromethyl, phenyl, 4-chlorophenyl, 2,4-dichlorophenyl, 4-nitrophenyl, 2,4-dinitrophenyl or pentafluorophenyl; and Y and Y' may be the same or different and are in the form of OH, OCOR'', OSO$_2$R'', and OCO$_2$R'', where R'' is a chromophore, fluorophore or electrophore capable of detection in chromatographic separation technology. Preferably R'' is 9-fluorenylmethyl (Fmoc), 5-dimethylaminonaphthalene (Dansyl), 7-methoxycoumarin, 6,7-dimethoxycoumarin, 7-dimethyl-aminocoumarin or 4-(dimethylamino)azobenzene (Dabsyl).

Functionalized solid phase oxime reagents of the present invention can be used to derivatize and detect compounds containing primary or secondary amines or thiol functionalities including amino acids, amino acid esters, peptides, polyamines, catecholamines, thiols or related species. The analytes are dissolved in a highly polar solvent such as N,N-dimethylformamide or dimethylsulfoxide and then contacted with the solid phase oxime reagents, either in batch or in a column. After a period of incubation the derivatized species, which now contains a detectable moiety (R'') transferred from the solid phase oxime reagent, is identified and quantitated by chromatographic methods known in the art.

The invention further relates to the preparation of solid phase reagents wherein the residual silanol activity associated with particulate silica gel or controlled pore glass has been effectively masked by application of a hydrophilic polymeric coating. This polymeric coating eliminates the irreversible adsorption of low molecular weight amines observed with prior art particulate silica gels or bonded phase silica gels which have not been functionalized in accordance with the present invention. This also eliminates the hydrophobic character associated with some bonded phase silica gels or bonded phase controlled pore glasses which can result in the irreversible adsorption of an analyte.

DETAILED DISCUSSION

Preparation of solid phase reagents

Silica gel suitable for use in preparing the solid phase reagents of this invention is any silica gel having an average particle diameter of from about 3 to 120 microns and an average pore size of from about 50 to 1000 Angstrom units. Such silica gel, consisting of amorphous silica, is commercially available in irregular and spherical particulate forms. Controlled pore glass (CPG) suitable for use in preparing solid phase reagents is any controlled pore glass having an average mesh size distribution of from about 20 to 400 mesh and an average pore size of from about 75 to 1000 Angstrom units.

Silica gel or controlled pore glass may be functionalized by reaction with 3-aminopropylthiethoxysilane. 3-aminopropyltrimethoxysilane, 4-aminobutyldimethylmethoxysilane or 4-aminobutyltriethoxysilane in anhydrous organic solvent at room temperature or at elevated temperature or by deposition from an aqueous solution at room temperature to yield aminoalkyl silica gel (APS) or aminoalkyl controlled pore glass (APG). Alternatively, aminopropyl silica gel or controlled pore glass is available commercially.

Polymeric(D,L-succinimide) of any molecular weight distribution soluble in N,N-dimethylformamide may be used for the functionalization of APS or CPG. For example poly(D,L-succinimide), formula II, of average molecular weight of 13,000 may be prepared by dehydration of D,L-aspartic acid at 190° C. for 50 hours (Alpert, A. J., J. Chromatogr., 266, 23 (1983)). Solubilization of poly(D,L-succinimide) in N,N-dimethylformamide and subsequent reaction with APS or APG at room temperature for 24 hours yields poly(D,L-succinimide)-silica, formula III. As shown in formula III and subsequent formulas, X is used to designate the particulate silica gel or controlled pore glass surface of the support.

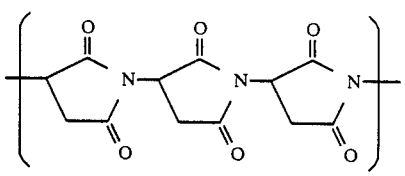

Formula II

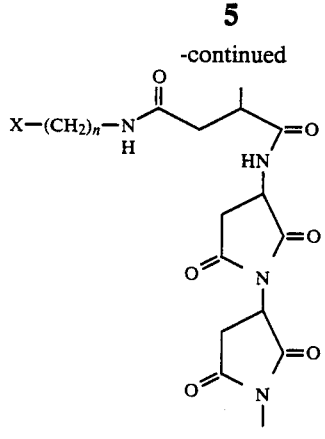

Formula III

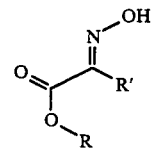

Further functionalization of poly(D,L-succinimide)-silica by reaction with a diamine or polyethyleneimine, such as, for example ethylenediamine, propylenediamine, butylenediamine, diethylenetriamine or triethylenetetraamine in N,N-dimethylformamide yields alpha-beta-poly(aminoalkyl or polyiminoalkyl D,L-aspartamide)-silica, formula IV, where n=1–6 and n'=3 or 4.

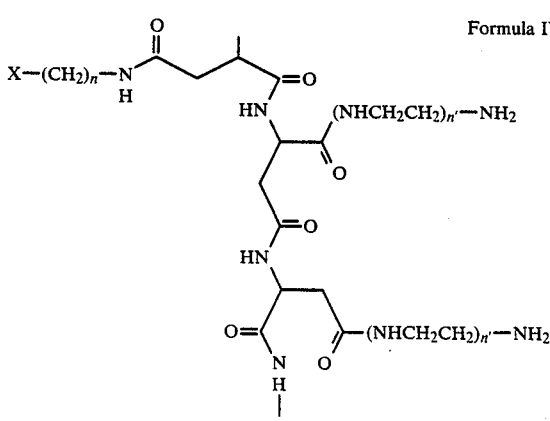

Formula IV

Reaction of a compound of formula IV with an oxime of general formula V wherein R is methyl, ethyl or the alcohol component of an activated ester, such as, for example, N-hydroxysuccinimide, pentafluorophenol, 2,4-dichlorophenol, 2-thiopyridyl or 4,6-dimethylpyrimidyl, and R' is an electron withdrawing substituent including, but not limited to cyano, trifluoromethyl, trichloromethyl, dichloromethyl, chloromethyl, phenyl, 4-chlorophenyl, 2,4-dichlorophenyl, 4-nitrophenyl, 2,4-dinitrophenyl or pentafluorophenyl, results in a solid phase oxime of general formula VI.

Formula V

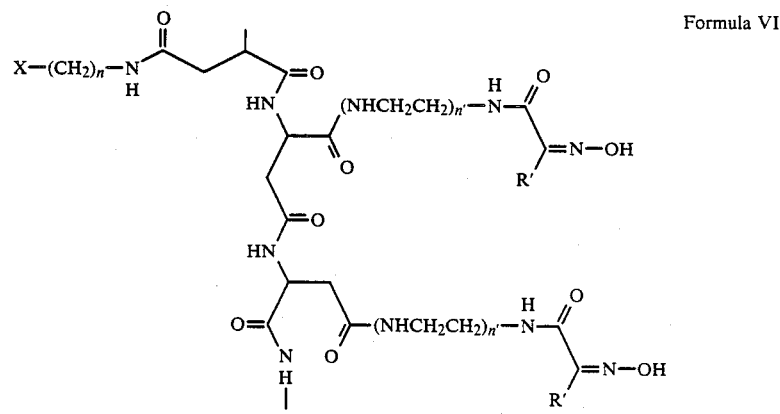

Formula VI

Reaction of a compound of general formula VI with a carboxylic acid chloride in the presence of an acid scavenger in N,N-dimethylformamide at low temperature or by reaction of a carboxylic acid after prior activation with diisopropylcarbodiimide in N,N-dimethylformamide at room temperature results in a solid phase activated ester of general formula VII wherein Y' may be either OCOR" or OH, and R" may be alkyl, aryl, alkyl/aryl or substituted aryl functionality, R" is the moiety which, in use, is transferred to the analyte, and is exploited as the basis for the subsequent separation and detection of the analyte.

Preferred R" moieties include those chromophores, fluorophores and electrophores which are known in the art as detectable moieties exploited in HPLC analyses in conjunction with ultraviolet, fluorescence and electrochemical detection including, but not limited to 9-fluorenylmethyl (Fmoc), 5-dimethylaminonaphthalene (Dansyl), 7-methoxycoumarin, 6,7-dimethoxycoumarin, 7-dimethylaminocoumarin, 4-(dimethylamino)azobenzene (Dabsyl), and others.

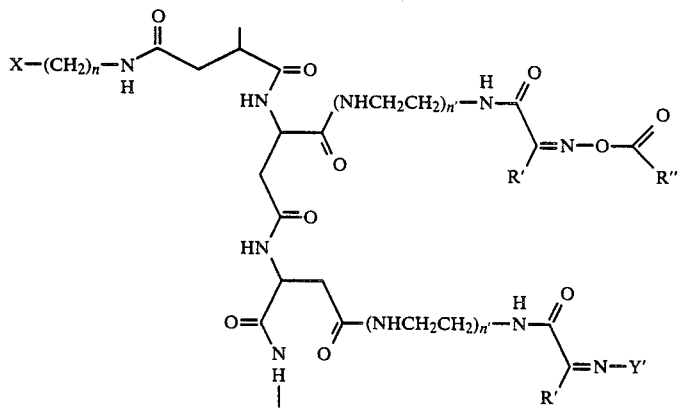

Formula VII

Reaction of a compound of general formula VI with a sulfonic acid chloride in the presence of an acid scavenger in N,N-dimethylformamide at low temperature (preferably 5° C. to 15° C.) results in a a solid phase activated ester of general formula VIII wherein Y' may be either $OSO_2R''$ or OH.

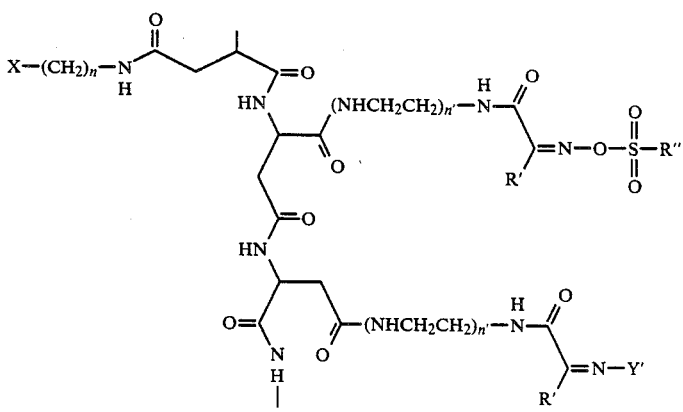

Formula VIII

Reaction of a compound of general formula VI with a chloroformate in the presence of an acid scavenger in N,N-dimethylformamide at low temperature, or through an intermediate dicyclohexylammonium salt of the compound of general formula VI in N,N-dimethylformamide at room temperature results in a solid phase activated carbonate of general formula IX wherein Y' may be either $OCO_2R''$ or OH.

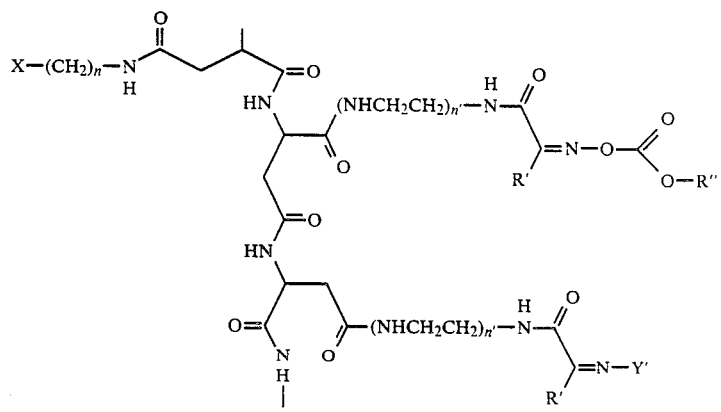

Formula IX

Use of solid phase reagents

Reaction of an amino acid, amino acid ester, peptide, polyamine, catecholamine, thiol or related species with a compound of general formula VII, VIII or IX (solid phase reagent), effected by preparing an analyte solution in N,N-dimethylformamide, ethanol, methanol, acetonitrile or and aqueous solution containing at least 50% N,N-dimethylformamide, ethanol, methanol or acetonitrile, buffered at a pH between 2 and 9. The analyte solution is brought into contact with the solid phase reagent either by adding the analyte solution to the solid phase reagent and allowing the mixture to stand a room temperature or at elevated temperature for several minutes with occasonal agitation, or preferably by packing the solid phase reagent in a column and pumping the analyte solution through the column at room temperature or at elevated temperature at a flow rate suitable to allow the analyte to contact the solid phase reagent for several minutes. The analyte solution containing the derivatized analytes, after a suitable period of incubation, is either filtered from the solid phase reagent or collected as the eluent from the solid phase reagent column.

After concentration of the derivatized analytes, an analysis is effected by high pressure liquid chromatography. The mode of detection employed is determined in accordance with the R" moiety associated with the solid phase reagent and transferred to the analyte during the derivatization reaction. The chromatographic analysis may involve normal phase, reverse phase, isocratic or gradient elution liquid chromatography. Chromophores, fluorophores and electrophores are known in the art as detectable moieties which are utilized in high pressure liquid chromatographic analyses in conjunction with ultraviolet, fluorescence and electrochemical detection.

The reaction of a compound of general formula VII with an amine to be detected would result in an amide containing the R" group. The reaction of a compound of general formula VIII with the amine would result in a sulfonamide containing the R" group. The reaction of a compound of general formula IX with the amine would result in a carbamate containing the R" group.

EXAMPLE I

Synthesis of poly(2-hydroxyimino-2-cyanoacetamidoethyl aspartamide)-silica (General formula VI)

Vydac 101TP silica gel (4.0 g) was weighed into a large test tube and covered with 5% (w/v) of 3-aminopropyltriethoxysilane in toluene (30 ml). The mixture was swirled with a vortex generator and kept under vacuum (with a one-hole stopper connected to a small pump) for 30 sec to remove air from the pores of the silica. The mixture was heated for 2 hours at 100° C. with occasional swirling. Aminopropyl-silica was collected in a medium-porosity scintered-glass funnel and washed with toluene (100 ml) and acetone (100 ml), then dried by continued suction.

D,L-Aspartic acid (50 g, 380 mmol) was deposited in a thin layer in a crystallization dish and heated in an oven at 190° C. for 50 hours. The resulting light tan powder weighed 37.9 g (indicating virtually quantitative dehydration, assuming a unit molecular weight of 97 for the product). The powder was dissolved with heating in 150 ml of N,N-dimethylformamide except for a small amount of white material. This was removed by centrifugation, leaving a brown solution. The product was collected by pouring the N,N-dimethylformamide solution into 4 volumes of ether, with rapid stirring, and collecting the precipitated product by centrifugation. The precipitate was freed of N,N-dimethylformamide by shaking it several times with ether followed by resedimentation. The precipitate was then dried in vacuo to yield a light tan powder, poly(succinimide) completely soluble in N,N-dimethylformamide.

Aminopropyl-silica (4.0 g) was added to 5% (w/v) of poly(succinimide) in N,N-dimethylformamide (20 ml). The mixture was swirled and degassed as described above, and then allowed to stand for 24 hours at room temperature with occasional swirling. The tan-colored product was collected in a medium-porosity scintered-glass funnel and washed with N,N-dimethylformamide (150 ml) and acetone (100 ml). The product was added to a solution containing ethylenediamine (0.25 ml, 3.7 mmol), ethylenediamine dihydrochloride (0.5 g, 3.7 mmol), water (4 ml) and N,N-dimethylformamide (20 ml). The mixture was again allowed to stand for 24 hours at room temperature with occasional swirling (this removes much of the tan color). The product was finally collected in a scintered-glass funnel and washed with water (200 ml), hydrochloric acid (150 ml, 0.05N), water (150 ml) and acetone (100 ml), then dried by continued suction to yield poly(aminoethyl aspartamide)-silica.

Ethylcyanoacetate (11.3 g, 100 mmol) is added to a solution of sodium nitrite (8.3 g, 120 mmol) in distilled water (50 ml) and acetic acid (8.0 ml=8.4 g, 140 mmol) is added to the stirred mixture. The ester disappears and soon yellow crystals of the sodium derivative start to separate. Next day the crystals are collected and then dissolved in 2N HCl (50 ml). The product is extracted with ether (four times, 50 ml each time) and the extracts dried over anhydrous $Na_2SO_4$. Removal of the solvent by evaporation in vacuo leaves a crystalline residue, ethyl 2-hydroxyimino-2-cyanoacetate, melting at 133° C. (12.4 g, 87%).

Ethyl 2-hydroxyimino-2-cyanoacetate (1.2 g, 8 mmol) was added to poly(aminoethyl aspartamide)-silica (4.0 g) in N,N-dimethylformamide (40 ml). The mixture was placed on an orbital shaker for 24 hours (100 rpm), then collected on a medium-porosity scintered-glass funnel and washed with N,N-dimethylformamide (100 ml), acetonitrile (50 ml), acetone (50 ml) and ether (50 ml), then dried by continued suction to yield poly(2-hydroxyimino-2-cyanoacetamidoethyl aspartamide)-silica.

EXAMPLE II

Synthesis of poly(2-oxyimino-2-cyanoacetamidoethyl aspartamide) 9-fluorenylmethylcarbonate-silica (General formula IX)

Poly(2-hydroxyimino-2-cyanoacetamidoethyl aspartamide)-silica (4.0 g) was added to a solution containing N,N-dicyclohexylamine (0.8 ml, 4 mmol) in N,N-dimethylformamide (40 ml). The mixture was placed on an orbital shaker for 12 hours (100 rpm), then collected in a medium-porosity scintered-glass funnel and washed with N,N-dimethylformamide (100 ml).

Dicyclohexylammonium poly(2-oxyimino-2-cyanoacetamidoethyl aspartamide)-silica (4.0 g) was added to a solution of 9-fluorenylmethylchloroformate (1.03 g, 4 mmol) in N,N-dimethylformamide (40 ml). The mixture was placed on an orbital shaker for one hour (100 rpm), then collected in a medium-porosity scintered-glass funnel and washed with N,N-dimethylformamide (100 ml), water (100 ml), $KHSO_4$ (100 ml, 0.1M), water (100 ml), acetone (50 ml) and ether (50 ml), then dried by continued suction to yield poly(2-oxyimino-2-cyanoacetamidoethyl aspartamide) 9-fluorenylmethylcarbonate-silica.

EXAMPLE III

Synthesis of poly(2-oxyimino-2-cyanoacetamidoethyl aspartamide) 5-N,N-dimethylaminonaphthalenesulfonate-silica General formula VIII)

Poly(2-hydroxyimino-2-cyanoacetamidoethyl aspartamide)-silica (4.0 g) was added to a solution containing 5-dimethylaminonaphthalenesulfonyl chloride (1.08 g, 4 mmol) and triethylamine (0.6 ml, 4.4 mmol) in N,N-dimethylformamide (40 ml). The mixture was placed on an orbital shaker for 3 hours (100 rpm) and the temperature maintained below 15° C. After allowing the mixture to warm the room temperatue the product was collected in a medium-porosity scintered-glass funnel and washed with N,N-dimethylformamide (100 ml), acetone (100 ml) and ether (50 ml), then dried by continued suction to yield poly(2-oxyimino-2-cyanoacetamidoethyl aspartamide) 5-N,N-dimethylaminonaphthalenesulfonate-silica.

EXAMPLE IV

Amino Acid Analysis

A sample containing 25 picomoles of amino acid standard (Pierce H Standard) was injected into a column containing approximately 1 gram of poly(2-oxyimio-2-cyanoacetamidoethyl aspartamide) 9-fluorenylmethylcarbonate-silica (3.0 mm×10 cm) at a flow rate of 50 μl/min. The solid phase reagent column is equilibrated for 15 min with 7:2:1 ethanol:acetonitrile:0.01M N-methylmorpholine trifluoroacetate buffer, pH 7.4, prior to injection. The eluent containing the derivatized amino acids was collected, evaporated to dryness, solubilized in acetone (20 μl) and subsequently analyzed by reverse phase high pressure liquid chromatography. The sample was resolved on a C18 column (4.6 mm×15 cm, 5μ) by ternary gradient elution (A=H$_2$O, 2.5 ml/liter acetic acid, 1.0 ml triethylamine, 0.5 ml trifluoroacetic acid, pH 3.1, B=850 ml H$_2$O containing 30 ml/liter acetic acid, 1.0 ml triethylamine, pH 4.5; add methanol to make 1 liter, C=acetonitrile) and detected by fluorescence (excitation @ 260 nm, emission cutoff filter @ 300 nm) according to the following protocol:

| Composition of Elution Gradient | | | |
|---|---|---|---|
| Time | % A | % B | % C |
| 0 | 75 | 0 | 25 |
| 11.5 | 60 | 0 | 40 |
| 14.0 | 60 | 0 | 40 |
| 14.1 | 0 | 65 | 35 |
| 18.0 | 0 | 55 | 45 |
| 25.0 | 0 | 25 | 75 |
| 30.0 | 0 | 25 | 75 |
| 30.1 | 75 | 0 | 25 |

An identical sample was derivatized by reaction with a 10-fold molar excess of 9-fluorenylmethylchloroformate in 2:1 borate buffer, pH 7.7 (0.2M):acetone. 9-Fluorenylmethanol resulting from hydrolysis of the chloroformate was removed by extraction with hexane (2 times, 1 ml each time). The results obtained for the solid phase reagent (Fmoc-SPR) and the homogeneous reaction with 9-fluorenylmethylchloroformate (Fmoc-CL) were as follows:

| Analysis of Amino Acid Standard | | | | |
|---|---|---|---|---|
| | Fmoc-Cl | Fmoc-SPR | | Fmoc-Cl | Fmoc-SPR |
| SER | 90% | 92% | PRO | 93% | 95% |
| ASP | 97% | 97% | MET | 97% | 97% |
| GLU | 96% | 98% | VAL | 98% | 96% |
| ARG | 87% | 85% | PHE | 96% | 98% |
| THR | 87% | 85% | ILE | 95% | 99% |
| ALA | 98% | 97% | LEU | 94% | 99% |
| TYR | 82% | 86% | HIS | 87% | 91% |
| GLY | 95% | 98% | LYS | 84% | 86% |

EXAMPLE V

Oxidized insulin A chain (2 mg/ml) was hydrolyzed in constant boiling 6N HCl vapor for 24 hours at 110° C. The sample was dissolved in 7:2:1 ethanol; water; triethylamine (1 ml) and dried in vacuo. The sample was then injected into a column of Fmoc-SPR at a flow rate of 50 μl/min and the eluant containing the derivatized amino acids collected. Chromatographic analysis as described above afforded the following results:

| Amino Acid Analysis of Oxidized Insulin A Chain | | | | |
|---|---|---|---|---|
| | Expected | Found | | Expected | Found |
| SER | 2 | 1.8 | PRO | 0 | — |
| ASP | 2 | 1.8 | MET | 0 | — |
| GLU | 4 | 3.7 | VAL | 2 | 1.8 |
| ARG | 0 | — | PHE | 0 | — |
| THR | 0 | — | ILE | 1 | 0.9 |
| ALA | 1 | 1.1 | LEU | 2 | 2.2 |
| TYR | 2 | 1.5 | HIS | 0 | — |
| GLY | 1 | 1.0 | LYS | 0 | — |

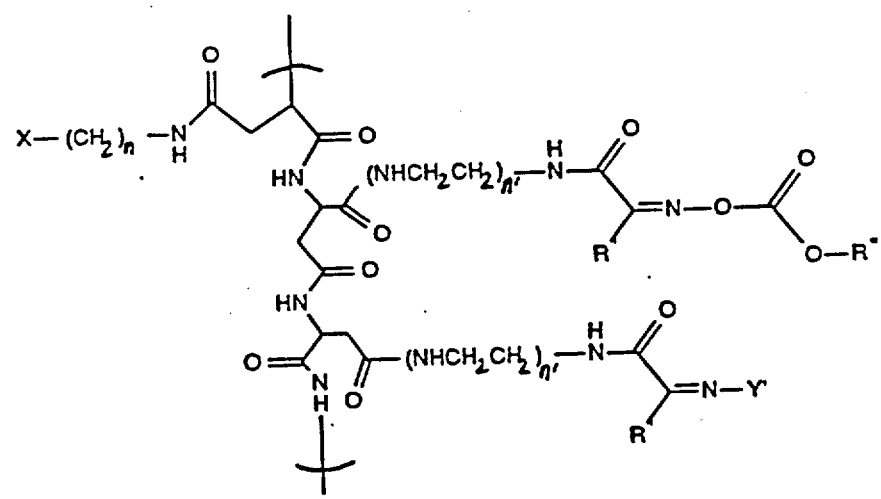
Formula IX (In the Abstract)
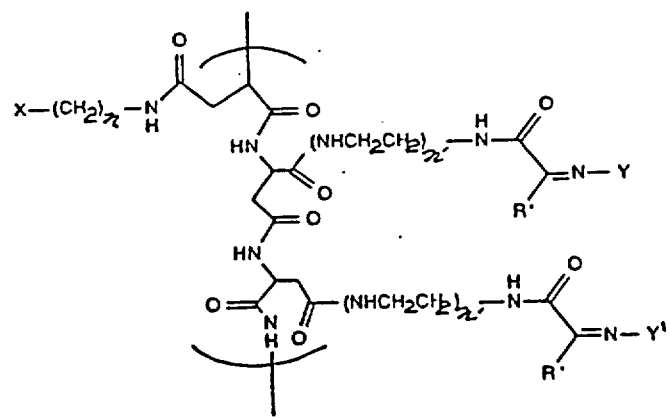

What is claimed is:

1. A solid phase oxime composition having the general formula I:

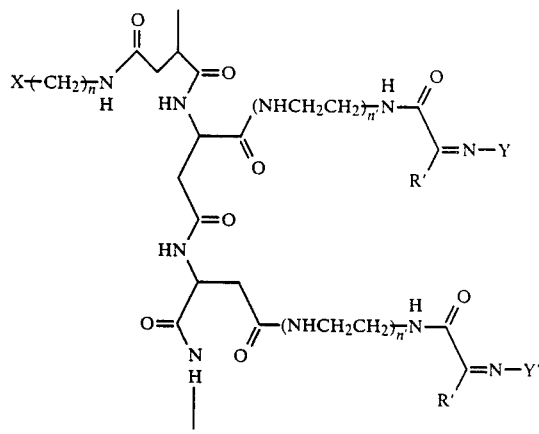

where X is particulate silica gel or controlled pore glass; n is 3 or 4, n' is 1-6; R' is an electron withdrawing group; and Y and Y' are selected from OH, OCOR", OSO$_2$R" or OCO$_2$R", where R" is a chromophore, fluorophore and electrophore.

2. The solid phase oxime composition of claim 1 wherein X is particulate silica gel having an average pore size distribution in the range of 120 to 500 Angstroms.

3. The solid phase oxime composition of claim 1 wherein n' is 2 or 3.

4. The solid phase oxime composition of claim 1 wherein R″ is selected from 9-fluorenylmethyl (Fmoc), 5-dimethylaminonaphthalene (Dansyl), 7-methoxycoumarin, 6,7-dimethoxycoumarin, 7-dimethylaminocoumarin or 4-(dimethylamino)azobenzene (Dabsyl).

5. The solid phase oxime composition of claim 1 wherein R′ selected from cyano, trifluoromethyl, trichloromethyl, dichloromethyl, chloromethyl, phenyl, 4-chlorophenyl, 2,4-dichlorophenyl, 4-nitrophenyl, 2,4-dinitrophenyl or pentafluorophenyl.

6. The solid phase oxime composition of claim 1 wherein X is particulate bonded silica having an average pore size distribution in the range of 120 to 500 Angstroms; n is 3; n′ is 1; R′ is selected from cyano and phenyl; and Y and Y′ are OH.

7. The solid phase oxime composition of claim 1 wherein X is particulate bonded silica having an average pore size distribution in the range of 120 to 500 Angstroms; n is 3; n′ is 1; R′ is selected from cyano or phenyl; and Y is selected from OH or $OSO_2R''$ and Y′ is $OSO_2R''$, where R″ is 5-dimethylaminonaphthalene.

8. The solid phase oxime composition of claim 1 wherein X is particulate bonded silica having an average pore size distribution in the range of 120 to 500 Angstroms; n is 3; n′ is 1; R′ is selected from cyano or phenyl; and Y is selected from OH or $OCO_2R''$ and Y′ is $OCO_2R''$, where R″ is 9-fluorenylmethyl.

9. A composition of the formula VI

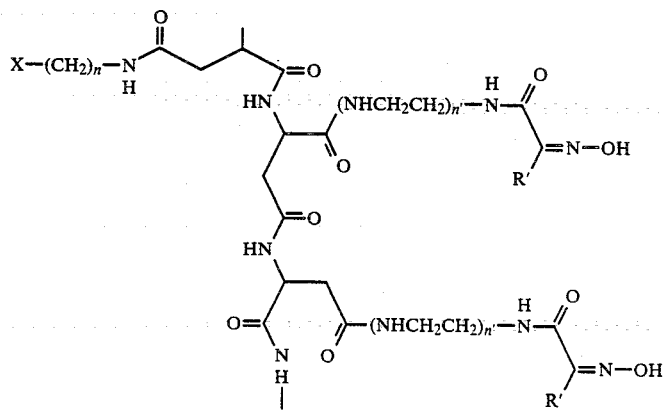

Formula VI where X is particulate bonded silica having an average pore size distribution in the range of 120 to 500 Angstroms, n is 3, n′ is 1, and R′ is selected from cyano and phenyl.

10. A composition of the formula VIII

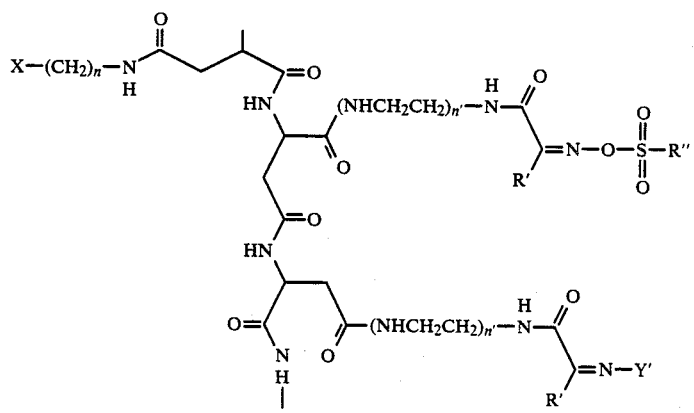

Formula VIII where X is particulate bonded silica having an average pore size distribution in the range of 120 to 500 Angstroms, n is 3, n′ is 1, and R′ is selected from cyano or phenyl, Y′ is selected from OH or $OSO_2R''$, where R″ is 5-dimethylaminonaphthalene.

11. A composition of the formula IX

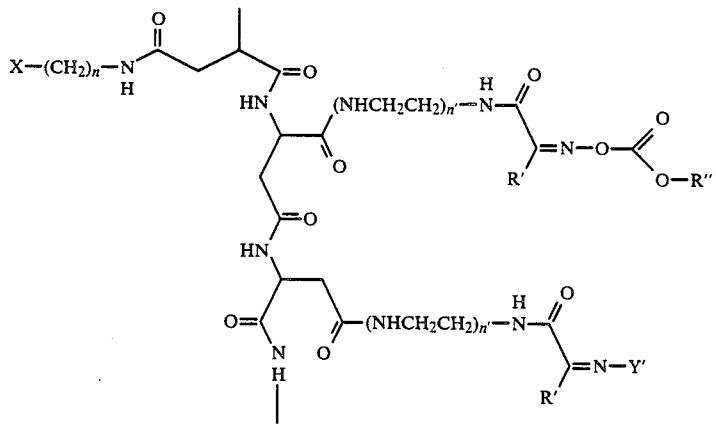

Formula IX where X is particulate bonded silica having an average pore size distribution in the range of 120 to 500 Angstroms, n is 3, n' is 1, and R' is selected from cyano or phenyl, Y' is selected from OH and OCO₂R'', where R'' is 9-fluorenylmethyl.

12. A method of making a solid phase oxime composition of the general formula I

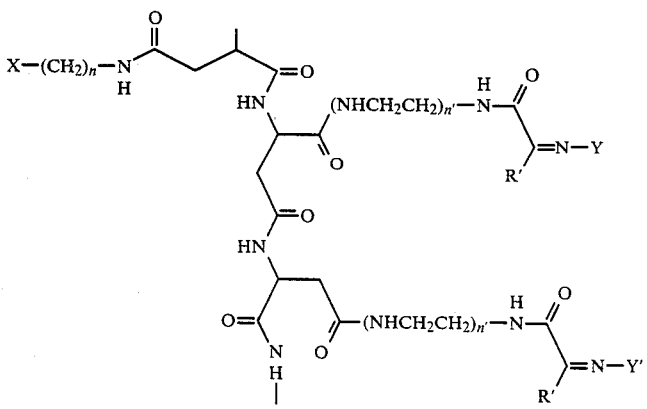

Formula I where X is particulate silica gel or controlled pore glass; n is 3 or 4, n' is 1–6: R' is an electron withdrawing group; and Y and Y' are selected from OH, OCOR'', OSO₂R'' and OCOOR'', where R''is a chromophore, fluorophore or electrophore, comprising the steps of:
reacting a solid phase support selected from alpha-beta-poly(polyiminoalkyl D,L-aspartamide)-silica or alpha-beta-poly(aminoalkyl D,L-aspartamide)-silica
with an oxime having the general formula V,

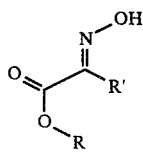

Formula V wherein R is methyl, ethyl or the alcohol component of an activated ester; and R' is an electron withdrawing substituent.

13. The method of claim 12 wherein R is selected from ethyl, methyl, N-hydroxysuccinimide, pentafluorophenol, 2,4-dichlorophenol, 2-thiopyridyl or 4,6-dimethyl-2-thiopyrimidyl.

14. The method of claim 13 wherein R is ethyl.

15. The method of claim 12 wherein R' is selected from cyano, trifluoromethyl, trichloromethyl, dichloromethyl, chloromethyl, phenyl, 4-chlorophenyl, 2,4-dichlorophenyl, 4-nitrophenyl, 2,4-dinitrophenyl or pentafluorophenyl.

16. The method of claim 15 wherein R' is selected from cyano or phenyl.

17. The method of claim 12 further comprising reacting the product of step b with a compound selected from R''COOCl, R''SO₂Cl, R''OCOCl, or R''COOH activated with a carbodiimide, wherein R'' is selected from a chromophore, fluorophore or electrophore.

18. The method of claim 17 wherein R'' is selected from 9-fluorenylmethyl (Fmoc), 5-dimethylaminonaphthalene (Dansyl), 7-methoxycoumarin, 6,7-dimethoxycoumarin, 7-dimethylaminocoumarin or 4-(dimethylamino)azobenzene (Dabsyl).

* * * * *

UNITED STATES PATENT AND TRADEMARK OFFICE
CERTIFICATE OF CORRECTION

PATENT NO. : 4,812,532

DATED : 3-14-89

INVENTOR(S) : Stolowitz

It is certified that error appears in the above-identified patent and that said Letters Patent is hereby corrected as shown below:

| Column | Line | |
|---|---|---|
| 3-4 | 1-18 | delete Formula I, insert revised Formula I (see attached sheet) |
| 5 | 1-40 | delete Formula III, insert revised Formula III (see attached) |
| 5 | 50-65 | delete Formula IV, insert revised Formula IV (see attached) |
| 5-6 | 15-35 | delete Formula VI, insert revised Formula VI (see attached) |
| 7-8 | 1-18 | delete Formula VII, insert revised Formula VII (see attached) |
| 7-8 | 21-39 | delete Formula IX, insert revised Formula IX (see attached) |
| 7-8 | 45-61 | delete Formula VIII, insert revised Formula VIII (see attached) |
| 12 | 40-57 | delete Formula I, insert revised Formula I (see attached) |
| 13-14 | 40-61 | delete Formula VIII, insert revised Formula VIII (see attached) |
| 13-14 | 10-31 | delete Formula VI, insert revised Formula VI (see attached) |
| 15-16 | 1-21 | delete Formula IX, insert revised Formula IX (see attached) |
| 15-16 | 28-44 | delete Formula I, insert revised Formula I (see attached) |

In the Abstract delete the formula, insert revised formula (see attached sheet)

Signed and Sealed this

Fifth Day of December, 1989

Attest:

JEFFREY M. SAMUELS

Attesting Officer     Acting Commissioner of Patents and Trademarks

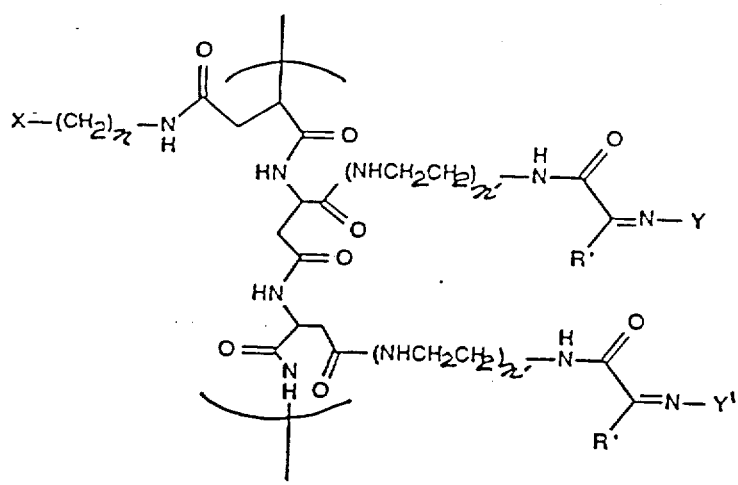
Formula I
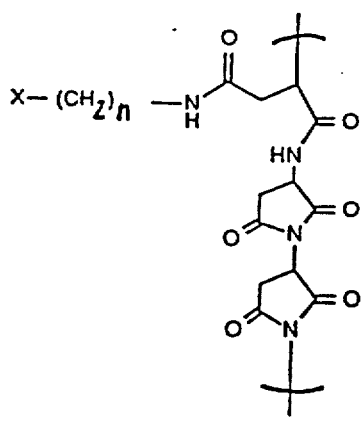
Formula III
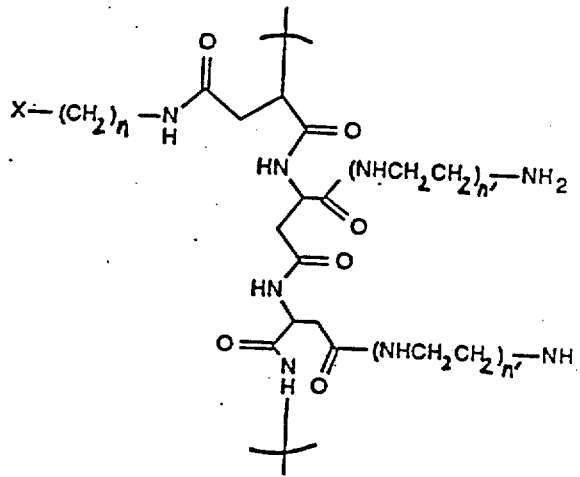
Formula IV

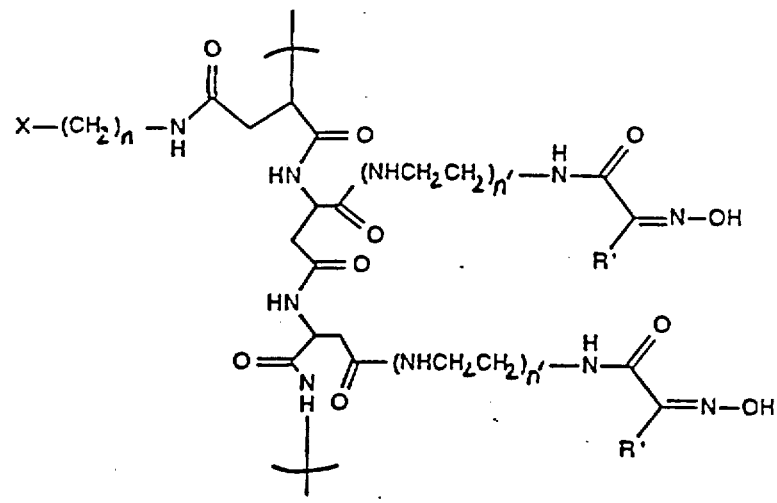
Formula VI

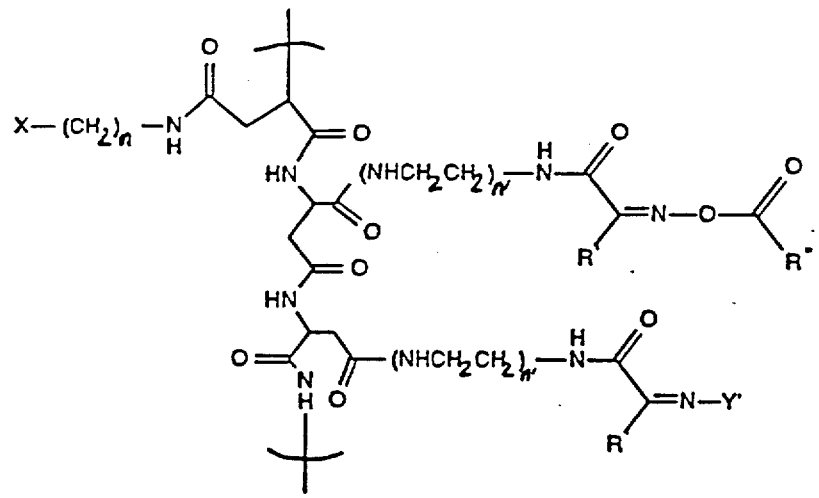
Formula VII
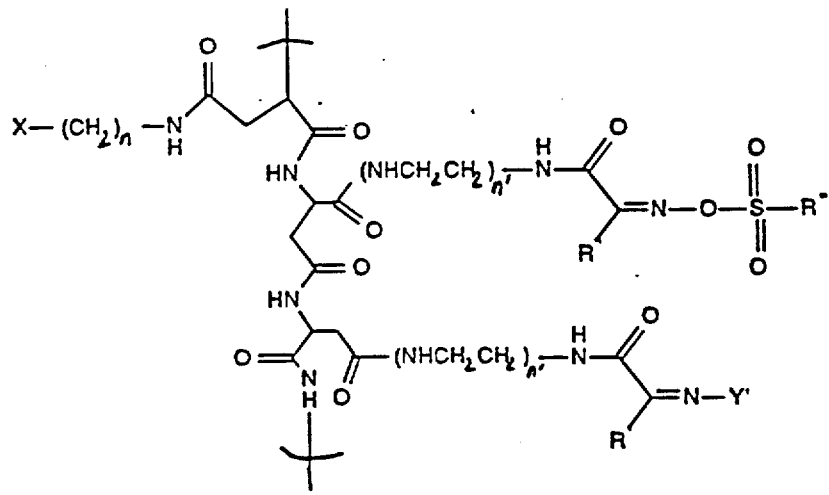
Formula VIII